(12) United States Patent
Shah et al.

(10) Patent No.: US 8,961,942 B2
(45) Date of Patent: Feb. 24, 2015

(54) SUNLESS TANNING COMPOSITIONS WITH ADJUVANTS COMPRISING SULFUR COMPRISING MOIETIES

(71) Applicant: Conopco, Inc., Englewood Cliffs, NJ (US)

(72) Inventors: Pravin Shah, Trumbull, CT (US); Joseph Oreste Carnali, Trumbull, CT (US); Qiang Qiu, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 227 days.

(21) Appl. No.: 13/669,898

(22) Filed: Nov. 6, 2012

(65) Prior Publication Data

US 2013/0149263 A1    Jun. 13, 2013

Related U.S. Application Data

(60) Provisional application No. 61/569,826, filed on Dec. 13, 2011.

(51) Int. Cl.
| | | |
|---|---|---|
| A61Q 17/04 | (2006.01) | |
| A61Q 19/04 | (2006.01) | |
| A61K 8/35 | (2006.01) | |
| A61K 8/46 | (2006.01) | |

(52) U.S. Cl.
CPC ............... *A61K 8/463* (2013.01); *A61Q 19/04* (2013.01)
USPC .......................................................... 424/59

(58) Field of Classification Search
None
See application file for complete search history.

(56) References Cited

U.S. PATENT DOCUMENTS

| | | | |
|---|---|---|---|
| 3,892,881 A | 7/1975 | Lissant | |
| 4,104,403 A | 8/1978 | Barker | |
| 4,246,285 A | 1/1981 | Van Duzee | |
| 4,385,049 A | 5/1983 | Cuca | |
| 4,405,616 A | 9/1983 | Rajadhyaksha | |
| 4,434,154 A * | 2/1984 | McShane | 424/60 |
| 4,446,051 A | 5/1984 | Berthod et al. | |
| 4,551,148 A | 11/1985 | Riley et al. | |
| 4,606,913 A | 8/1986 | Aronson | |
| 4,808,610 A | 2/1989 | Munayyer et al. | |
| 4,886,783 A | 12/1989 | Minaskanian | |
| 4,888,783 A | 12/1989 | Kojima | |
| 4,981,845 A | 1/1991 | Pereira | |
| 5,118,845 A | 6/1992 | Peck | |
| 5,131,911 A | 7/1992 | Lang et al. | |
| 5,232,688 A | 8/1993 | Ziegler et al. | |
| 5,387,417 A | 2/1995 | Rentsch | |
| 5,412,004 A | 5/1995 | Tachibana | |
| 5,489,429 A | 2/1996 | Griat et al. | |
| 5,523,075 A | 6/1996 | Fuerst et al. | |
| 5,612,044 A | 3/1997 | Suares et al. | |
| 5,645,822 A | 7/1997 | Meyere et al. | |
| 5,700,452 A | 12/1997 | Deckner et al. | |
| 5,705,145 A | 1/1998 | Miklean et al. | |
| 5,720,948 A | 2/1998 | Brucks | |
| 5,750,092 A | 5/1998 | Meyer et al. | |
| 5,756,075 A | 5/1998 | Meyer | |
| 5,814,659 A | 9/1998 | Elden | |
| 5,827,506 A | 10/1998 | McShane et al. | |
| 5,833,973 A | 11/1998 | Dobkowski | |
| 5,908,707 A | 6/1999 | Cabell | |
| 5,977,194 A | 11/1999 | Mork | |
| 6,033,648 A | 3/2000 | Candau | |
| 6,060,041 A | 5/2000 | Candau et al. | |
| 6,069,169 A | 5/2000 | Ptchelintsev et al. | |
| 6,147,131 A | 11/2000 | Mork | |
| 6,231,837 B1 | 5/2001 | Stroud et al. | |
| 6,303,834 B1 | 10/2001 | Mork | |
| 6,313,181 B1 | 11/2001 | Cohen | |
| 6,326,033 B1 | 12/2001 | Darmenton et al. | |
| 6,352,701 B1 | 3/2002 | Scholz et al. | |
| 6,383,503 B1 | 5/2002 | Bleckmann | |
| 6,399,046 B1 | 6/2002 | Schonrock et al. | |
| 6,423,326 B1 | 7/2002 | Shapiro | |
| 6,423,626 B1 | 7/2002 | Srinivasan et al. | |
| 6,475,500 B2 | 11/2002 | Vatter | |
| 6,524,598 B2 | 2/2003 | Sunkel | |
| 6,548,050 B1 | 4/2003 | Bara | |
| 6,645,474 B1 | 11/2003 | Galdi et al. | |
| 6,685,952 B1 | 2/2004 | Ma et al. | |
| 6,696,049 B2 | 2/2004 | Vatter | |
| 6,699,488 B2 | 3/2004 | Deckner | |
| 6,747,115 B2 | 6/2004 | Sakuta | |
| 6,793,929 B2 | 9/2004 | Bleckmann | |
| 7,166,276 B2 | 1/2007 | Stephens et al. | |
| 7,175,835 B1 | 2/2007 | Simoulidis et al. | |

(Continued)

FOREIGN PATENT DOCUMENTS

| | | |
|---|---|---|
| CN | 1816316 A | 8/2006 |
| CN | 101068528 A | 5/2011 |

(Continued)

OTHER PUBLICATIONS

English Abstract from SciFinder of CN 101204361 A, original document published Jun. 25, 2008.*
English Abstract from SciFinder of Kohno et al. Nippon Keshohin Gijutsusha Kaishi, 31(4) p. 455-460, 1997.*
Original Japanese article Kohno et al. Nippon Keshohin Gijutsusha Kaishi, 31(4) p. 455-460, 1997.*
PCT International Search Report PCT/EP2012/072894 dated Jun. 24, 2013.
Carbopol® Aqua SF-1 Polymer, Lubrizol Technical Data Sheet, Feb. 7, 2013, pp. 1-9.

(Continued)

*Primary Examiner* — Nissa Westerberg
(74) *Attorney, Agent, or Firm* — Edward A. Squillante, Jr.

(57) ABSTRACT

Sunless tanning compositions with adjuvants comprising sulfur comprising moieties are described. The compositions comprise an adjuvant with a +6 oxidation state sulfur moiety and results in excellent artificial tanning results within a consumer acceptable time.

9 Claims, No Drawings

(56) References Cited

U.S. PATENT DOCUMENTS

| | | | |
|---|---|---|---|
| 7,316,808 B2 | 1/2008 | Candau | |
| 7,416,735 B2 | 8/2008 | El-Nokaly et al. | |
| 7,462,363 B2 | 12/2008 | Braun | |
| 7,807,188 B2 | 10/2010 | Hoath et al. | |
| 8,241,614 B2 | 8/2012 | Carnali | |
| 8,299,127 B2 | 10/2012 | Anjing | |
| 8,398,959 B2 | 3/2013 | Yang et al. | |
| 8,425,882 B2 | 4/2013 | Lou et al. | |
| 2002/0028184 A1 | 3/2002 | Sunkel | |
| 2002/0028223 A1 | 3/2002 | Vatter et al. | |
| 2002/0051755 A1 | 5/2002 | Candau et al. | |
| 2002/0106385 A1 | 8/2002 | Vatter | |
| 2002/0142018 A1 | 10/2002 | Scholz et al. | |
| 2003/0021815 A9 | 1/2003 | Mondet et al. | |
| 2003/0044365 A1 | 3/2003 | Candau | |
| 2003/0049212 A1 | 3/2003 | Robinson et al. | |
| 2003/0082119 A1 | 5/2003 | Golz-Berner et al. | |
| 2003/0108498 A1 | 6/2003 | Stephens et al. | |
| 2003/0170193 A1 | 9/2003 | Pate | |
| 2003/0211061 A1 | 11/2003 | Deckner | |
| 2003/0211069 A1 | 11/2003 | Deckner | |
| 2003/0228339 A1 | 12/2003 | El-Nokaly et al. | |
| 2004/0014653 A1 | 1/2004 | Smith | |
| 2004/0047819 A1 | 3/2004 | Hansenne et al. | |
| 2004/0076597 A1 | 4/2004 | Berens et al. | |
| 2004/0086474 A1 | 5/2004 | Rabe et al. | |
| 2004/0091437 A1 | 5/2004 | Fack et al. | |
| 2004/0146472 A1 | 7/2004 | Nakanishi | |
| 2004/0185072 A1 | 9/2004 | Hitzel et al. | |
| 2004/0208903 A1 | 10/2004 | Robinson et al. | |
| 2004/0228821 A1 | 11/2004 | Sunkel et al. | |
| 2004/0235693 A1 | 11/2004 | Wei | |
| 2005/0002978 A1 | 1/2005 | Crook et al. | |
| 2005/0008600 A1 | 1/2005 | Nakanishi | |
| 2005/0089486 A1 | 4/2005 | Spindler | |
| 2005/0118218 A1 | 6/2005 | Cassin | |
| 2005/0163812 A1 | 7/2005 | Hoath et al. | |
| 2005/0169856 A1 | 8/2005 | Grollier | |
| 2005/0175570 A1 | 8/2005 | Inoue | |
| 2005/0191326 A1 | 9/2005 | Meiker | |
| 2005/0238595 A1 | 10/2005 | Stella | |
| 2006/0008426 A1 | 1/2006 | Doring | |
| 2006/0013790 A1 | 1/2006 | Shimizu | |
| 2006/0057927 A1 | 3/2006 | Kang | |
| 2006/0078524 A1 | 4/2006 | Midha | |
| 2006/0078527 A1 | 4/2006 | Midha et al. | |
| 2006/0079417 A1 | 4/2006 | Wagner et al. | |
| 2006/0079422 A1 | 4/2006 | Midha | |
| 2006/0100004 A1 | 5/2006 | Kim et al. | |
| 2006/0111490 A1 | 5/2006 | Fonolla Moreno | |
| 2006/0120979 A1 | 6/2006 | Rubin | |
| 2006/0127344 A1 | 6/2006 | Zofchak | |
| 2006/0171909 A1 | 8/2006 | Morrissey et al. | |
| 2007/0009463 A1 | 1/2007 | Niebauer | |
| 2007/0020217 A1 | 1/2007 | Themens | |
| 2007/0067924 A1 | 3/2007 | Beck et al. | |
| 2007/0173599 A1 | 7/2007 | Liu | |
| 2007/0231355 A1 | 10/2007 | Quadir et al. | |
| 2007/0292373 A1 | 12/2007 | Russ et al. | |
| 2008/0081057 A1 | 4/2008 | Chevalier | |
| 2008/0279793 A1 | 11/2008 | Rudolph et al. | |
| 2008/0279796 A1 | 11/2008 | Handrosch et al. | |
| 2008/0299058 A1 | 12/2008 | Saito | |
| 2008/0299156 A1 | 12/2008 | Fares et al. | |
| 2008/0311058 A1 | 12/2008 | Lou | |
| 2008/0317693 A1 | 12/2008 | Ricard | |
| 2009/0035241 A1 | 2/2009 | Cassin | |
| 2009/0041688 A1 | 2/2009 | Dueva-Koganov et al. | |
| 2009/0155321 A1 | 6/2009 | Harichian et al. | |
| 2009/0155322 A1 | 6/2009 | Harichian et al. | |
| 2009/0155373 A1 | 6/2009 | Huang et al. | |
| 2009/0178209 A1 | 7/2009 | Koike et al. | |
| 2009/0226498 A1 | 9/2009 | Flugge-Berendes | |
| 2009/0247445 A1 | 10/2009 | Lou et al. | |
| 2009/0280147 A1 | 11/2009 | Alberius et al. | |
| 2010/0035783 A1 | 2/2010 | Restrepo et al. | |
| 2010/0209364 A1 | 8/2010 | Abe et al. | |
| 2010/0310483 A1 | 12/2010 | Klug et al. | |
| 2011/0150802 A1 | 6/2011 | Bui et al. | |
| 2011/0150805 A1 | 6/2011 | Kergosien et al. | |
| 2011/0150807 A1 | 6/2011 | Bui et al. | |
| 2011/0286942 A1 | 11/2011 | Lou | |
| 2011/0305649 A1 | 12/2011 | Lou | |
| 2011/0305651 A1 | 12/2011 | Carnali | |
| 2012/0039967 A1 | 2/2012 | Lou | |
| 2012/0100083 A1 | 4/2012 | Carnali | |
| 2012/0141393 A1 | 6/2012 | Yang | |
| 2012/0189676 A1 | 7/2012 | Susak et al. | |

FOREIGN PATENT DOCUMENTS

| | | |
|---|---|---|
| DE | 4122033 A1 | 1/1993 |
| DE | 10049041 | 4/2002 |
| DE | 10049041 A1 | 4/2002 |
| DE | 102004055541 | 5/2006 |
| DE | DE102004055541 A1 | 5/2006 |
| DE | 102007013368 | 9/2008 |
| DE | DE102007013368 A1 | 9/2008 |
| DE | 102008006857 | 1/2009 |
| EP | GB1465530 | 2/1974 |
| EP | 0009404 B1 | 2/1984 |
| EP | 0160430 | 11/1985 |
| EP | 0302147 A1 | 2/1989 |
| EP | 0456545 | 11/1991 |
| EP | 0456545 A1 | 11/1991 |
| EP | 0500446 A | 8/1992 |
| EP | 0500446 A1 | 8/1992 |
| EP | 810181 A2 | 12/1997 |
| EP | 818190 | 1/1998 |
| EP | 1210933 A1 | 6/2002 |
| EP | 1352639 A1 | 10/2003 |
| EP | 1581660 A1 | 12/2004 |
| EP | 1600144 A1 | 11/2005 |
| EP | 1741422 | 1/2007 |
| EP | 1849498 A2 | 10/2007 |
| EP | 2087879 | 8/2009 |
| EP | 2087879 A | 8/2009 |
| EP | 2380557 A1 | 10/2011 |
| EP | 1864647 B | 11/2011 |
| EP | 1864647 B1 | 11/2011 |
| FR | 2651126 | 3/1991 |
| FR | 2651126 A1 | 3/1991 |
| FR | 2894468 A1 | 12/2005 |
| GB | 1420299 A | 1/1976 |
| GB | 1465528 | 2/1977 |
| GB | 1465529 | 2/1977 |
| GB | 2139919 | 11/1984 |
| GB | 2181737 | 4/1987 |
| GB | 2224754 A | 5/1990 |
| JP | 57091733 | 6/1982 |
| JP | 1281140 A | 11/1989 |
| JP | 11158032 | 6/1999 |
| JP | 2004107249 A | 4/2004 |
| JP | 2005314327 | 11/2005 |
| JP | 2007326813 | 12/2007 |
| JP | 2007326813 A | 12/2007 |
| WO | WO9217159 A2 | 10/1992 |
| WO | WO9403148 A2 | 2/1994 |
| WO | WO9415580 A1 | 7/1994 |
| WO | WO9421221 A1 | 9/1994 |
| WO | WO9526178 | 10/1995 |
| WO | WO9621721 | 7/1996 |
| WO | WO9733560 | 9/1997 |
| WO | WO9800098 A1 | 1/1998 |
| WO | WO9955303 A1 | 11/1999 |
| WO | WO0100141 | 1/2001 |
| WO | WO0107003 A1 | 2/2001 |
| WO | 0128552 A2 | 4/2001 |
| WO | WO0189464 | 11/2001 |
| WO | WO03022235 | 3/2003 |
| WO | WO03075879 | 9/2003 |
| WO | WO03080005 A1 | 10/2003 |
| WO | WO03086339 A1 | 10/2003 |
| WO | WO2004105721 A1 | 12/2004 |

(56) References Cited

FOREIGN PATENT DOCUMENTS

| WO | WO2005004833 A1 | 1/2005 |
|---|---|---|
| WO | WO2005016302 A1 | 2/2005 |
| WO | WO2005025505 A2 | 3/2005 |
| WO | WO2006018149 A1 | 2/2006 |
| WO | WO2006102289 A2 | 9/2006 |
| WO | WO2007064687 A1 | 6/2007 |
| WO | WO2008013757 A2 | 1/2008 |
| WO | WO2008018046 A2 | 2/2008 |
| WO | WO2008155228 | 12/2008 |
| WO | WO2009014061 A1 | 1/2009 |
| WO | WO2009053287 A1 | 4/2009 |
| WO | WO2009074513 A1 | 6/2009 |
| WO | WO2009083545 A2 | 7/2009 |
| WO | WO2009121787 | 10/2009 |
| WO | WO2010009989 | 1/2010 |
| WO | WO2010045163 | 4/2010 |
| WO | WO2011075871 A1 | 6/2011 |
| WO | WO2011090821 A2 | 7/2011 |
| WO | WO2011157640 A2 | 12/2011 |

OTHER PUBLICATIONS

Shin-Etsu-Silicone for Personal Care, Shin-Etsu Chemical Co., Ltd., 2004, pp. 1-6.
Dussaud et al., "Liquid Transport in the Networked Microchannels of the Skin Surface", Langmuir, 2003, vol. 19, pp. 7341-7345.
"Cyclomethicone and Essential Oils", Lotioncrafter, pp. 1-3.
Shin Etsu Silicone, "Silicone Products for Personal Care-Shin-Etsu Unique Materials", ShinEtsu Silicone, 2007, pp. 1-20.
PCT International Search Report in PCT application PCT/EP2009/053578 dated Jul. 29, 2009 with Written Opinion.
PCT International Search Report in PCT application PCT/EP2011/059661 dated Jul. 10, 2012 with Written Opinion.
PCT International Search Report in PCT application PCT/CN2010/000864 dated Mar. 24, 2011 with Written Opinion.
GB Search Report in GB application GB1113318.8 dated Nov. 7, 2011.
GB Search Report in GB application GB1116661.8 dated Jan. 16, 2012.
Application: Applicant: Lou et al.; Co-pending U.S. Appl. No. 12/060,437, filed Apr. 1, 2008.
Application: Applicant: Lou et al., Co-pending U.S. Appl. No. 12/784,046, filed May 20, 2010.
Application: Applicant: Lou et al., Co-pending U.S. Appl. No. 12/814,855, filed Jun. 14, 2010.
Application: Applicant: Carnali et al., Co-pending U.S. Appl. No. 13/155,451, filed Jun. 8, 2010.
Application: Applicant: Lou et al., Co-pending U.S. Appl. No. 13/155,451, filed Aug. 12, 2010.
Application: Applicant: Carnali et al., Co-pending U.S. Appl. No. 12/909,874, filed Oct. 22, 2010.
Wikipedia, "Microemulsion"—Retrieved online Feb. 7, 2014—4 pages.

* cited by examiner

SUNLESS TANNING COMPOSITIONS WITH ADJUVANTS COMPRISING SULFUR COMPRISING MOIETIES

FIELD OF THE INVENTION

The present invention is directed to a composition and method for imparting a sunless tan to skin. More particularly, the invention is directed to a composition and method that employ a sunless tanning agent as well as an adjuvant for the sunless tanning agent. The composition employs an adjuvant comprising a +6 oxidation state sulfur moiety, is stable, and when applied, unexpectedly results in the consumer having skin with a brownish/tan coloration within a consumer acceptable time.

BACKGROUND OF THE INVENTION

Sunless tanning agents are typically formulated into two types of cosmetic products. Of these, the most traditional is the self-tanning lotion. The imparted benefit is to achieve a skin coloration equivalent to that from basking in the sun. More recently, a second product category has arrived. Therein a sunless tanning agent in small amounts is added to a typical moisturizing lotion. A "glow or shine" is thereby imparted. Glow or shine is a major factor in the appearance of healthy looking skin.

Prominent among the sunless tanning agents is dihydroxyacetone ("DHA" which is also chemically known as 1,3-dihydroxy-2-propanone). DHA, after application, is believed to exert its effect through interactions between its carbonyl group and the amino groups of amino acids and peptides naturally occurring in the hydrolipid pellicle and first layers of the stratum corneum of the skin. These so-called Maillard reactions are believed (see, e.g., Bobin et al., J. Soc. Cosmet. Chem. 35: 255 (1984)) to lead to formation of brown pigments in the skin, thereby giving skin an appearance similar to that of a naturally obtained tan. A number of other sunless tanning agents have been identified, including melanin, mahakanni (eclipta alba), methyl glyoxal, erythrulose, alloxan, 2,3-dihydroxysuccindialdehyde, mixtures thereof, or the like. These agents are believed to work in a similar way as DHA, but typically do yield somewhat of their own unique pigmentation.

Unfortunately, many sunless tanning products available on the market are not stable in that they turn a yellow and/or orange color after application, especially when exposed to UV light. Other sunless tanning products perform poorly and do not quickly impart a noticeable brown color after application. Such poorly performing products do not prevent "tan-happy" consumers from basking in the sun. Products that underperform, therefore, do not protect consumers from the sun's ultraviolet rays.

There is increasing interest to develop compositions and methods for imparting a sunless tan, and especially, compositions that are storage stable. This invention, therefore, is directed to a composition and method that employ a sunless tanning agent as well as an adjuvant for the sunless tanning agent. The composition employs an adjuvant comprising a +6 oxidation state sulfur moiety and, when applied, unexpectedly results in the consumer having skin with a brownish/tan coloration within a consumer acceptable time.

Additional Information

Efforts have been disclosed for making self-tanning cosmetic compositions. In U.S. Pat. Nos. 5,232,688 and 5,612,044, self-tanner compositions with DHA are described.

Other efforts have been disclosed for making self-tanning compositions. In U.S. Pat. No. 5,750,092, compositions with DHA and secondary amines are described.

Still other efforts have been disclosed for making self-tanning compositions. In U.S. Pat. No. 6,231,837, self tanning formulations comprising DHA, polyethoxyglycol and a polyol are described. In U.S. Pat. No. 5,756,075, a self tanning method is disclosed in which a fluid comprising DHA can be mixed with a complimentary fluid comprising specific primary amines.

None of the additional information describes a composition and/or method that yield excellent sunless tanning results whereby the composition and method employ a sunless tanning agent and an adjuvant comprising a +6 oxidation state sulfur moiety.

SUMMARY OF THE INVENTION

In a first aspect, the present invention is directed to a composition comprising:
  a) a sunless tanning agent; and
  b) an adjuvant for the sunless tanning agent, the adjuvant comprising a +6 oxidation state sulfur moiety.

In a second aspect, the present invention is directed to a method for generating a sunless tan comprising the step of applying to the skin the composition of the first aspect of this invention.

All other aspects of the present invention will more readily become apparent upon considering the detailed description and examples which follow.

Sunless tanning, as used herein, means obtaining the suntan look by applying a topical composition. The same can be interchanged with self-tanning. Composition, as used herein, is meant to include a substance applied to a human body for imparting a sunless tan where the composition is for example, an end use leave-on skin lotion, cream or mouse, shampoo, hair conditioner, shower gel, toilet bar, body wash, shaving cream, body wax, depilatory, mascara, sunscreen product or the like. Such a composition may also be put on, body towelettes for application to the body. In a preferred embodiment, the composition of this invention is a lotion or cream. Consumer acceptable time means within about 3 to about 6 hours from application, and preferably, from about 3 to about 4 hours, and most preferably, from about 1 to about 2 hours subsequent to application. Stable means at least about 60%, and preferably, at least about 85% by weight of the sunless tanning agent in the composition does not result in formation of color bodies after about twenty (20) days of storage at about 35° C. and when formulated as a monophase product with adjuvant and at a pH in a range from 3 to 6. Adjuvant comprising a +6 oxidation state sulfur moiety means an adjuvant comprising the moiety —$OSO_2OR$ where R is H, a $C_{1-3}$ alkyl or aryl.

Comprising, as used herein, is meant to include consisting essentially of and consisting of. For the avoidance of doubt, the adjuvant used in this invention can be one that consists essentially of or consists of adjuvant comprising a +6 oxidation state sulfur moiety. All ranges identified herein are meant to include all ranges subsumed therein if, for example, reference to the same is not explicitly made.

DETAILED DESCRIPTION OF THE INVENTION

The sunless tanning agent suitable for use in this invention is only limited to the extent that the same may be applied topically on humans to form pigmented components. Such materials may be alpha-hydroxyaldelydes and ketones, glyceraldehyde, troxerutin and related alcohol aldehydes, various indoles, imidazoles and derivatives thereof.

Illustrative yet non-limiting examples of the sunless tanning agents that may be used in this invention include dihydroxyacetone, melanin, mahakanni (eclipta alba), methyl glyoxal, erythrulose, alloxan, 2,3-dihydroxysuccindialdehyde, mixtures thereof, or the like. In a preferred embodiment, the sunless tanning agent used is dihydroxyacetone, erythrulose, alloxan, or a mixture thereof. In a most preferred embodiment, the sunless tanning agent is dihydroxyacetone.

Typically, the sunless tanning agent makes up from about 0.025 to about 35%, and preferably, from about 0.05 to about 15%, and most preferably, from about 0.5 to about 10% by weight of the composition, based on total weight of the composition and including all ranges subsumed therein.

The adjuvant that may be used in this invention is limited only to the extent that the same may be used in a composition suitable for topical application to humans.

Typically, the adjuvant is one comprising a compound having the formula:

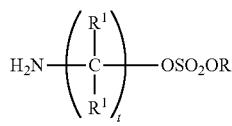

I where R is H, a $C_{1-3}$ alkyl or aryl, each $R^1$ is independently H or a $C_{1-10}$ substituted or unsubstituted alkyl group, and t is an integer from about 1 to about 10.

In an especially preferred embodiment, the sunless tanning adjuvant used in this invention is one comprising w-aminoalkyl hydrogen sulfate, and most preferably, 2-aminoethyl hydrogen sulfate. Typically, the adjuvant makes up from about 0.025 to about 35%, and preferably, from about 0.05 to about 15%, and most preferably, from about 0.5 to about 8% by weight of the composition, including all ranges subsumed therein.

It is also within the scope of this invention to employ mixtures of additional adjuvants for use with the adjuvant comprising a +6 oxidation state sulfur moiety. Such additional adjuvants are limited only to the extent they are compatible with the adjuvant comprising a +6 oxidation state sulfur moiety and suitable for use in topical compositions.

Illustrative examples of the additional adjuvants that may be used in this invention include those having the formula:

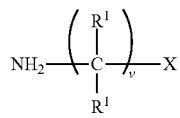

II where X is —S—$CR^2_3$,

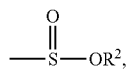

or $SO_2OR^2$, each $R^1$ is as previously defined, each $R^2$ is independently H, $C_{1-3}$ alkyl or aryl and v is an integer from about 1 to about 10.

In an especially preferred embodiment, the additional adjuvant employed is a ω-methylthio alkylamines like 2-methylthio ethylamine, hypotaurine, taurine or a mixture thereof. In another especially preferred embodiment, the adjuvant used in this invention is at least about 35% by weight, and preferably, from about 50 to about 100%, and most preferably, from about 75 to about 100% by weight, ω-aminoalkyl hydrogen sulfate based on total weight of adjuvant in the composition and including all ranges subsumed therein.

Compositions of the present invention will typically include a cosmetically acceptable carrier. Water is the most preferred carrier. Amounts of water may range from about 1 to about 99%, and preferably, from about 5 to about 90%, and most preferably, from about 35 to about 80% and optimally from about 40 to about 75% by weight, based on total weight of the composition and including all ranges subsumed therein. Ordinarily the compositions will be water arid oil emulsions, most preferably, of the oil-in-water variety. Water-In-oil emulsions, and especially, those generally classified as water-in-oil and high internal phase emulsions are, however, an option. Illustrative examples of the high internal phase emulsions suitable to carry the actives and adjuvants of this invention are described in commonly owned U.S. Patent Application Publication Nos. 2008/0311058 and 2009/0247445, the disclosures of which are incorporated herein by reference.

Other cosmetically acceptable carriers may include mineral oils, silicone oils, synthetic or natural esters, fatty acids and alcohols. Amounts of these materials may range from about 0.1 to about 50%, and preferably, from about 0.1 to about 30%, and most preferably, from about 1 to about 20% by weight of the composition, including all ranges subsumed therein.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, and preferably, from about 4 to about 5 silicon atoms.

Linear volatile silicone materials generally have viscosities of less than about 5 centistokes at 25° C. while cyclic materials typically have viscosities of less than about 10 centistokes.

Nonvolatile silicone oils useful as carrier material induce polyalkyl siloxanes, polyalkylaryl siloxanes and polyether siloxane copolymers. The essentially non-volatile polyalkyl siloxanes useful herein include, for example, polydimethylsiloxanes (like dimethicone) with viscosities of from about 5 to about 100,000 centistokes at 25° C.

An often preferred silicone source is a cyclopentasiloxane and dimethiconol solution.

Among suitable esters are:
(1) Alkenyl or alkyl esters of fatty acids having 10 to 20 carbon atoms like isopropyl palmitate, isopropyl isostearate, isononyl isononanoate, oleyl myristate, oleyl stearate, and oleyl oleate;
(2) Ether-esters such as fatty acid esters of ethoxylated fatty alcohols;
(3) Polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty add esters, and polyoxyethylene sorbitan fatty add esters;

(4) Wax esters such as beeswax, spermaceti, myristyl myristate, stearyl stearate; and (5) Sterol esters, of which soya sterol and cholesterol fatty acid esters are examples thereof.

Fatty acids having from 10 to 30 carbon atoms may be included in the compositions of this invention. Illustrative, of this category are pelargonic, lauric, myristic, palmitic, stearic, isostearic, hydroxystearic, oleic, linoleic, ricinoleic, arachidic, behenic and erucic adds.

Emulsifiers may be present in the compositions of the present invention. Total concentration of the emulsifier may range from about 0.1 to about 40%, and preferably, from about 1 to about 20%, and most preferably, from about 1 to about 5% by weight of the composition, including all ranges subsumed therein. The emulsifier may be selected from the group consisting of anionic, nonionic, cationic and amphoteric actives. Particularly preferred nonionic actives are those with a $C_1$-$C_{20}$ fatty alcohol or add hydrophobe condensed with from about 2 to about 100 moles of ethylene oxide or propylene oxide per mole of hydrophobe, $C_2$-$C_{10}$ alkyl phenols condensed with from 2 to 20 moles of alkylene oxide; mono- and di-fatty acid esters of ethylene glycol; fatty acid monoglyceride, sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic emulsifiers.

Preferred anionic emulsifiers include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, alkylethercarboxylates and combinations thereof.

Cationic emulsifiers that may be used include, for example, palmitamidopropyltrimonium chloride, distearyldimonium chloride and mixtures thereof. Useful amphoteric emulsifiers include cocoamidopropyl betaine, $C_{12}$-$C_{20}$ trialkyl betaines, sodium lauroamphoacetate, and sodium laurodiamphoacetate or a mixture thereof.

Other generally preferred emulsifiers include glyceryl stearate, glycol stearate, stearamide AMP, PEG-100 stearate, cetyl alcohol as well as emulsifying/thickening additives like hydroxyethylacrylate/sodium acryloyldimethyl taurates copolymer/squalane and mixtures thereof.

Preservatives can desirably be incorporated into the compositions comprising the sunless tanning agent and adjuvant of this invention to protect against the growth of potentially harmful microorganisms. Suitable traditional preservatives for compositions of this invention are alkyl esters of parahydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition, including all ranges subsumed therein.

Thickening agents may be included in compositions of the present invention. Particularly useful are the polysaccharides. Examples include starches, natural/synthetic gums and cellulosics. Representative of the starches are chemically modified starches such as sodium hydroxypropyl starch phosphate and aluminum starch octenylsuccinate. Tapioca starch is often preferred. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are yet another class of effective thickening agent. This category includes crosslinked polyacrylates such as the Carbomers, polyacrylamides such as Sepigel® 305 and taurate copolymers such as Simugel EG® and Aristoflex® AVC, the copolymers being identified by respective INCI nomenclature as Sodium Acrylate/Sodium Acryloyldimethyl Taurate and Acryloyl Dimethyltaurate/Vinyl Pyrrolidone Copolymer. Another preferred synthetic polymer suitable for thickening is an acrylate-based polymer made commercially available by Seppic and sold under the name Simulgel INS100.

Amounts of the thickener may range from about 0.001 to about 5%, and preferably, from about 0.1 to about 2%, and most preferably, from about 0.2 to about 0.5% by weight of the composition including all ranges subsumed therein.

Fragrances, fixatives and abrasives may optionally be included in compositions of the present invention. Each of these substances may range from about 0.05 to about 5%, preferably between 0.1 and 3% by weight.

To enhance skin moisturization, cationic ammonium compounds may optionally be used in the compositions of this invention. Such compounds include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono(hydroxyethyl) ammonium salts, guar hydroxypropyl trimonium salts, 2,3-dihydroxypropyltri($C_1$-$C_3$ alkyl or hydroxalkyl) ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from about 0.01 to about 30%, and preferably, from about 0.1 to about 15% by weight of the composition.

When cationic ammonium compounds are used, preferred additives for use with the same are moisturizing agents such as substituted ureas like hydroxymethyl urea, hydroxyethyl urea, hydroxypropyl urea; bis(hydroxmethyl) urea; bis(hydroxyethyl) urea, bis(hydroxypropyl) urea, N,N'-dihydroxymethyl urea, N,N'-di-hydroxyethyl urea, N,N'-di-hydroxypropyl urea, N,N,N'-tri-hydroxyethyl urea; tetra (hydroxymethyl) urea, tetra(hydroxyethyl) urea; tetra (hydroxypropyl) urea, N-methyl-N'-hydroxyethyl urea; N-ethyl-N,N—N'-hydroxyethyl urea; N-hydroxypropyl-N'-hydroxyethyl urea and N,N'-dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Amounts of substituted urea, when used, in the composition of this invention range from about 0.01 to about 20%, and preferably, from about 0.5 to about 15%, and most preferably, from about 2 to about 10% based on total weight of the composition and including all ranges subsumed therein.

Conventional humectants may be employed in the present invention. These are generally polyhydric alcohol-type materials. Typical polyhydric alcohols include glycerol glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.5 to 20%, preferably between 1 and 15% by weight of the composition.

When cationic ammonium compound and substituted urea are used, in a most especially preferred embodiment at least from about 1 to about 15% glycerin is used, based on total weight of the composition and including all ranges subsumed therein.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the composition.

Desquamation promoters may be present. Illustrative are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic adds. Amounts of these materials when present may range from about 0.01 to about 15% by weight of the composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, yarrow, chamomile, licorice, aloe vera, grape seed, citrus unshul, willow bark, sage, thyme and rosemary.

Also optionally suitable for use include materials like sunscreens as well as lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Conventional buffers/pH modifiers may be used. These include commonly employed additives like sodium hydroxide, hydrochloric acid, citric acid and citrate/citric acid buffers. In an especially preferred embodiment, the pH of the composition of this invention is from about 3 to about 6, and preferably, from about 3.25 to about 4.75, and most preferably, from about 3.25 to about 4, including all ranges subsumed therein.

Colorants, opacifiers, chelators (like tetrasodium EDTA) and abrasives may also be included in the compositions of the present invention. Each of these substances may range from about 0.05 to about 5%, preferably between 0.1 and 3% by weight of the composition.

In an especially preferred embodiment, the composition of the present invention comprises less than about 5%, and preferably, from 0.01 to 4% by weight glycine, and most preferably, no glycine.

A wide variety of packaging can be employed to store and deliver the compositions. Packaging is often dependent upon the type of personal care end-use. For instance, leave-on skin lotions and creams, shampoos, conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered in a stick composition formulation in a container with propel-repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film.

Example 1

In vitro performance of adjuvants including those within the scope of this invention was assessed by contacting the same (at the molar equivalent of 1% glycine) with 2.5% dihydroxyacetone, Color change was noted in terms of $\Delta E^*$ after certain time frames. Commercially available Vitro-Skin® (synthetic skin) was used as the substrate and pH of the adjuvant and dihydroxyacetone formulations were maintained at 3.5, adjusted with citric acid.

TABLE 1

| | ($\Delta E^*$ reported at Time Frames) | | | |
|---|---|---|---|---|
| Sample | Adjuvant | 5.5 Hours | 29 Hours | 53 Hours |
| 1 | None | 6.0 | 19.0 | 23.0 |
| 2 | Glycine | 15.5 | 33.0 | 37.0 |
| 3 | 2-Methylthio-Ethylamine | 22.0 | 32.0 | 36.0 |
| 4 | Hypotaurine | 8.0 | 21.0 | 26.0 |
| 5 | Taurine | 17.0 | 33.0 | 36.0 |
| 6 | 2-Aminoethyl Hydrogen Sulfate | 20.0 | 35.0 | 39.0 |

The formulations above that were applied to the synthetic skin all resulted in coloration. The synthetic skin was pre-hydrated at 95% Relative Humidity (RH) for about 24 hours and then treated with formulations at a dosage of 5 μl/cm². The treated synthetic skin was stored at 35° C. and 40% RH for certain time frames, not exceeding 53 hours. Color development was monitored periodically after treatment using a HunterLab Labscan XE colorimeter. $\Delta E^*$ is defined as $\sqrt{[(\Delta L^*)^2+(\Delta a+)^2+(\Delta b^*)^2]}$ where $\Delta L^*$ is lightness change, $\Delta a^*$ is the change in +red/−green, $\Delta b^*$ is the change in +red/−blue and further where smaller $\Delta E^*$ indicates less color change.

The results shown in Table 1 unexpectedly show that adjuvants consistent with this invention surprisingly accelerate and enhance coloration by dihydroxyacetone on in vitro substrate. Unexpectedly, such color enhancement is at least as successful as color enhancement with glycine.

Example 2

The following end-use compositions were made by mixing the ingredients below under conditions of moderate shear, atmospheric pressure and ambient temperature.

TABLE 2

| Ingredient | Sample (% by weight) Sample 7 |
|---|---|
| Sodium hydroxypropyl starch phosphate | 0.10 |
| Chelator | 0.11 |
| Preservative | 0.3 |
| Glycerin | 12.0 |
| Citric acid* | 0.1-0.2 |
| Colorant | 0.19 |
| Stearic acid | 1.97 |
| Emulsifier | 4.2 |
| Cetyl alcohol | 0.31 |
| Isopropyl palmitate | 2.25 |
| Silicone oil | 1.5 |
| Phenoxyethanol | 0.4 |
| fragrance | 0.35 |
| Dihydroxyacetone | 2.5 |
| 2-aminoethyl hydrogen sulfate | 1.0 |
| 2-methylthio ethyl amine | 0.0 |
| taurine | 0.0 |
| Deionized water | balance |

*to pH of about 3.3

TABLE 3

| Ingredients | Sample (% by weight) Sample 8 |
|---|---|
| Thickening agent | 0.25 |
| Tapioca starch | 0.5 |
| Chelator | 0.05 |
| Preservative | 0.3 |
| Glycerin | 12.0 |
| Citric acid* | 0.02 |
| Colorant | 0.19 |
| Glyceryl stearate | 2.4 |
| PEG 100 stearate | 1.2 |
| Cetyl alcohol | 2.4 |
| Isopropyl palmitate | 2.0 |
| Wax | 1.0 |
| Dimethicone 50 cst | 3.0 |
| Phenoxyethanol | 0.4 |
| Fragrance | 0.35 |
| Dihydroxyacetone | 2.5 |
| 2-aminoethyl hydrogen sulfate | 1.0 |
| 2-methylthio ethyl amine | 0.0 |
| taurine | 0.0 |
| Deionized water | to 100 |

*to pH of about 3.3

Both sample 7 and 8 were applied to synthetic skin in a manner similar to the one described in Example 1. The results obtained surprisingly revealed a ΔE* after 50 hours of about 40, indicating that the adjuvants of the present invention perform well with dihydroxyacetone in end-use compositions with different base ingredients.

Example 3

The short term benefits of the inventive additives on the speed-to-tan was appraised in vivo by following color development over the course of several hours. Twenty test subjects were chosen for study based on a pre-screening criteria of having a pale complexion free of complexities in the study area. Three 5×5 $cm^2$ sites were located on each forearm of each subject and 0.05 mL of a product corresponding either to Sample 7 with or without 1% adjuvant was applied by a skilled technician to each site. Sample 7 without adjuvant is the Control. Each subject thus had three application sites of product described in Sample 7 with adjuvant and three application sites of the control. Application was made in the morning and color development at the site followed using the procedure described in Example 1. The measurement protocol was as follows:

15 minute acclimation period following subject arrival at the testing center

Baseline measurement

Product application

First measurement at 55 minutes

Second measurement at 110 minutes

Third measurement at 165 minutes

Fourth measurement at 220 minutes

Fifth measurement at 310 minutes

Sixth measurement at 365 minutes

Seventh measurement at 410 minutes

The measured ΔL* is interpreted so that negative values signify decreased lightness.

TABLE 4

| Sample Time (min) | Control, balance to water ΔL* | Sample 7 ΔL* |
|---|---|---|
| 0 | 0.0 | 0.0 |
| 55 | 0.2 | 0.1 |
| 110 | −0.5 | −0.9 |
| 165 | −1.4 | −2.1 |
| 220 | −2.7 | −3.6 |
| 310 | −3.1 | −4.1 |
| 365 | −3.5 | −4.4 |
| 410 | −3.9 | −4.9 |

Entries for Sample 7 gave statistically significant darkening ($p<0.05$) relative to the same product without adjuvant. Surprisingly, the data in Table 4 shows the product of Sample 7 (with adjuvant) outperformed the adjuvant-free Control product at multiple time points over multiple test sites on the subjects. Significantly darker color development was noted less than two hours after product application and the enhanced darkening was consistently maintained over the course of 7 hours after application. This example demonstrates that the adjuvants of this invention deliver a consumer perceivable tanning enhancement on a time scale as short as two hours.

Example 4

It was unexpectedly discovered that mixtures of the inventive adjuvant with optional adjuvants could give a superior coloration action relative to either taken separately. When, for example, equal mole mixtures of taurine and 2-aminoethyl hydrogen sulfate are combined at a total level equivalent to 1% glycine, the observations recorded in Table 5 were made.

TABLE 5

| Adjuvant | ΔE* | | |
|---|---|---|---|
| | 5 hours | 21 hours | 46 hours |
| 2-Aminoethyl Hydrogen Sulfate | 15 | 25 | 27 |
| Taurine | 9 | 26 | 28 |
| 2-Aminoethyl Hydrogen Sulfate/Taurine Mixture | 15 | 32 | 35 |

The formulations were assessed for color change (ΔE*) as described above and it was surprisingly observed that the mixture gave superior coloration to either adjuvant taken separately at a level which is the molar equivalent to 1% glycine, dihydroxyacetone at 2.5%, pH with citric acid at 3.5.

What is claimed is:

1. A composition comprising:
   a) a sunless tanning agent comprising dihydroxyacetone; and
   b) an adjuvant for the sunless tanning agent that is 2-aminoethyl hydrogen sulfate.

2. The composition according to claim 1 wherein the composition comprises, in addition to 2-aminoethyl hydrogen sulfate, adjuvant comprising a compound having the formula:

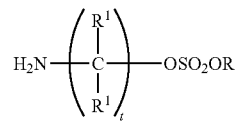

I where R is H, a $C_{1-3}$ alkyl or aryl, each $R^1$ is independently H or a $C_{1-10}$ substituted or unsubstituted alkyl group, and t is an integer from about 1 to about 10.

3. The composition according to claim 1 wherein the sunless tanning agent further comprises, erythrulose, alloxan, methyl glyoxal, mahakanni, melanin, 2,3-dihydroxysuccindialdehyde or a mixture thereof.

4. The composition according to claim 1 wherein the composition further comprises 2-methylthio ethylamine, hypotaurine, taurine, or a mixture thereof.

5. The composition according to claim 1 wherein the adjuvant makes up from about 0.025 to about 35% by weight of the composition, and the sunless tanning agent makes up from about 0.025 to about 35% by weight of the composition.

6. The composition according to claim 1 wherein the composition further comprises preservative, thickening agent, fragrance, cationic ammonium compound, sunscreen, substituted urea, vitamin or a mixture thereof.

7. The composition according to claim 1 wherein the composition is a leave-on sunless tanning lotion.

8. A method for imparting a sunless tan to skin comprising the step of applying to skin the composition of claim 1.

9. The method according to claim 8 wherein the composition further comprises sunscreen.

* * * * *